United States Patent
Landi et al.

(10) Patent No.: US 10,555,561 B2
(45) Date of Patent: Feb. 11, 2020

(54) ATHLETIC GARMENT WITH INTEGRAL CUP ASSEMBLY

(71) Applicant: SHOCK DOCTOR, INC., Minnetonka, MN (US)

(72) Inventors: James J. Landi, Maplewood, NJ (US); Michael T. Landi, Glen Ridge, NJ (US)

(73) Assignee: Shock Doctor, Inc., Fountain Valley, CA (US)

( * ) Notice: Subject to any disclaimer, the term of this patent is extended or adjusted under 35 U.S.C. 154(b) by 0 days.

(21) Appl. No.: 15/463,301

(22) Filed: Mar. 20, 2017

(65) Prior Publication Data

US 2017/0251730 A1 Sep. 7, 2017

Related U.S. Application Data

(63) Continuation of application No. 13/551,881, filed on Jul. 18, 2012, now Pat. No. 9,629,395, which is a
(Continued)

(51) Int. Cl.
*A41B 9/02* (2006.01)
*A41B 9/12* (2006.01)
(Continued)

(52) U.S. Cl.
CPC .............. *A41B 9/12* (2013.01); *A41B 9/004* (2013.01); *A41B 9/02* (2013.01); *A41D 1/088* (2013.01); *A41D 13/015* (2013.01); *A41D 13/0506* (2013.01); *A41D 13/0525* (2013.01); *A41D 13/0575* (2013.01); *A61F 13/70* (2013.01);
(Continued)

(58) Field of Classification Search
CPC ........ A41D 1/08; A41D 1/088; A41D 13/015; A41D 13/05; A41D 13/0525; A41D 13/0575; A41D 13/0506; A41D 13/0593; A41D 13/0581; A41D 13/0556; A41D 13/0562; A41D 13/0568; A41B 9/001;
(Continued)

(56) References Cited

U.S. PATENT DOCUMENTS 756,666 A    4/1904   Lustig
849,471 A    4/1907   Gamble
(Continued)

FOREIGN PATENT DOCUMENTS

CA    1290098 E    10/1991
CA    2756359 A1 * 10/2012    ......... A41D 13/0575
FR    945501 A   *  5/1949    ............... A41B 9/02

OTHER PUBLICATIONS

Canadian Office Action dated Apr. 4, 2013 for Application No. 2,756,359.
(Continued)

*Primary Examiner* — Jameson D Collier
(74) *Attorney, Agent, or Firm* — Faegre Baker Daniels LLP

(57) ABSTRACT

An athletic garment generally includes a short member, a supporter, and a plurality of straps. The short member may include a front panel, rear panel, two side panels, and a waistband. The supporter is dimensioned to releasably receive an athletic protective cup. The straps are coupled to one end of the supporter and are attached to the opposing rear panel of the short member.

3 Claims, 8 Drawing Sheets

Related U.S. Application Data continuation-in-part of application No. 13/357,955, filed on Jan. 25, 2012, now Pat. No. 9,629,400.

(60) Provisional application No. 61/479,566, filed on Apr. 27, 2011.

(51) Int. Cl.
| | |
|---|---|
| *A41D 13/015* | (2006.01) |
| *A61F 13/70* | (2006.01) |
| *A41B 9/00* | (2006.01) |
| *A41D 13/05* | (2006.01) |
| *A63B 71/12* | (2006.01) |
| *A41D 1/08* | (2018.01) |
| *A61F 13/15* | (2006.01) |

(52) U.S. Cl.
CPC ............ *A63B 71/1216* (2013.01); *A61F 2013/15121* (2013.01); *A63B 2209/10* (2013.01)

(58) Field of Classification Search
CPC .. A41B 9/004; A41B 9/02; A41B 9/08; A41B 9/12; A41B 9/023; A63B 71/1216
USPC .............................................. 2/400–405, 466
See application file for complete search history.

(56) References Cited

U.S. PATENT DOCUMENTS

| | | | |
|---|---|---|---|
| 903,472 A | 11/1908 | Huddleston | |
| 1,250,407 A | 12/1917 | Woods | |
| 1,381,254 A | 6/1921 | Thorp | |
| 1,421,077 A | 6/1922 | Goldsmith | |
| 1,477,565 A | 12/1923 | Jenkins | |
| 1,492,504 A | 4/1924 | Blume | |
| 1,688,676 A | 10/1928 | Whitley | |
| 1,720,439 A | 7/1929 | Richardson | |
| 1,830,572 A | 11/1931 | Taylor | |
| 1,866,220 A | 7/1932 | Norton | |
| 1,919,299 A | 7/1933 | Levin | |
| 1,990,403 A | 2/1935 | Davitt | |
| 2,255,931 A | 9/1941 | Kloster | |
| 2,283,684 A | 5/1942 | Matthews | |
| 2,396,599 A | 3/1946 | O'brien | |
| 2,522,375 A | 9/1950 | Jones et al. | |
| 2,700,971 A | 2/1955 | Mestel | |
| 2,713,340 A | 7/1955 | Meminger | |
| 2,854,973 A | 10/1958 | Jackson | |
| 3,176,686 A | 4/1965 | Barnes | |
| 3,229,692 A | 1/1966 | Creed | |
| 3,499,443 A | 3/1970 | Scheerer | |
| 3,714,946 A | 2/1973 | Rudes | |
| 3,782,375 A | 1/1974 | Donars | |
| 3,787,892 A | 1/1974 | Quinn | |
| 3,788,314 A | 1/1974 | Noreen | |
| 3,797,501 A | 3/1974 | Di Tullio | |
| 3,963,022 A * | 6/1976 | Rotello | A61F 5/40 602/70 |
| D246,011 S | 10/1977 | Eckman | |
| 4,134,400 A | 1/1979 | DiMatteo | |
| 4,141,357 A | 2/1979 | Dietz | |
| 4,156,294 A | 5/1979 | Horn | |
| D252,116 S | 6/1979 | DiMatteo | |
| 4,257,414 A | 3/1981 | Gamm et al. | |
| 4,285,069 A | 8/1981 | Hall | |
| 4,453,541 A | 6/1984 | Castelli et al. | |
| 4,471,772 A | 9/1984 | Miller, Jr. | |
| 4,484,360 A | 11/1984 | Leighton et al. | |
| 4,587,675 A | 5/1986 | Prouty | |
| 4,619,055 A | 10/1986 | Davidson | |
| 4,660,554 A | 4/1987 | Wright | |
| 4,698,847 A | 10/1987 | Yoshihara | |
| D294,075 S | 2/1988 | Bernstein | |
| 4,811,427 A | 3/1989 | Regan | |
| 4,870,958 A | 10/1989 | Webster | |
| 4,922,899 A | 5/1990 | Graff et al. | |
| 4,967,768 A | 11/1990 | Tatro | |
| 4,989,594 A | 2/1991 | Doherty et al. | |
| 5,020,547 A | 6/1991 | Strock | |
| 5,070,869 A | 12/1991 | Zhang | |
| 5,157,793 A | 10/1992 | Michels | |
| 5,210,882 A | 5/1993 | Moretz et al. | |
| 5,239,706 A | 8/1993 | Stevenson | |
| 5,243,974 A | 9/1993 | Allen | |
| 5,274,854 A | 1/1994 | Wenner et al. | |
| 5,275,592 A * | 1/1994 | Grizzaffi | A61F 5/4401 2/403 |
| 5,301,370 A | 4/1994 | Henson | |
| 5,405,312 A | 4/1995 | Jacobs | |
| D364,262 S | 11/1995 | Magidson et al. | |
| 5,479,942 A | 1/1996 | DiMatteo | |
| 5,499,404 A | 3/1996 | Marchiorello | |
| 5,557,804 A | 9/1996 | Ovortrup et al. | |
| D389,289 S | 1/1998 | Law | |
| D395,735 S | 7/1998 | Paramore | |
| 5,819,323 A | 10/1998 | Edenfield | |
| 5,876,395 A | 3/1999 | Hart et al. | |
| 5,920,914 A | 7/1999 | Dempsey | |
| 6,023,789 A | 2/2000 | Wilson et al. | |
| 6,041,441 A | 3/2000 | Counts et al. | |
| 6,048,327 A | 4/2000 | Kieffer | |
| 6,058,514 A | 5/2000 | Hart | |
| 6,061,832 A | 5/2000 | Morrison, Jr. | |
| 6,076,195 A | 6/2000 | Klein | |
| 6,287,169 B1 | 9/2001 | Willms et al. | |
| 6,319,219 B1 | 11/2001 | Landi | |
| D453,604 S | 2/2002 | Hart | |
| D457,690 S | 5/2002 | Griffiths | |
| 6,430,753 B2 | 8/2002 | Duran | |
| 6,537,132 B1 | 3/2003 | Alberts | |
| 6,701,533 B2 | 3/2004 | Webb | |
| 6,918,140 B1 | 7/2005 | Cooper | |
| 6,979,325 B2 | 12/2005 | Reddy | |
| 7,004,921 B2 | 2/2006 | Littell | |
| 7,100,213 B2 | 9/2006 | Krautbauer | |
| 7,178,176 B1 | 2/2007 | S-Cronenbold | |
| 7,216,371 B2 | 5/2007 | Wong | |
| D548,928 S | 8/2007 | Wong | |
| 7,296,307 B2 | 11/2007 | Atwater et al. | |
| D572,430 S | 7/2008 | Wong | |
| 7,404,216 B1 * | 7/2008 | Paramore | A63B 71/1216 2/406 |
| 7,712,156 B2 | 5/2010 | Raber | |
| 7,716,755 B1 | 5/2010 | Wiens | |
| 7,757,307 B2 | 7/2010 | Wong | |
| 7,757,310 B2 | 7/2010 | Wong | |
| 7,900,285 B2 | 3/2011 | Steszyn et al. | |
| 7,937,767 B2 | 5/2011 | Leach et al. | |
| 8,336,120 B2 | 12/2012 | Wong | |
| 8,887,316 B2 | 11/2014 | Wong | |
| 9,301,560 B2 | 4/2016 | Wong | |
| 9,629,395 B2 | 4/2017 | Landi et al. | |
| 9,629,400 B2 | 4/2017 | Landi et al. | |
| 2003/0051288 A1 | 3/2003 | Dugan | |
| 2003/0163076 A1 | 8/2003 | Lukens | |
| 2003/0167557 A1 | 9/2003 | LaShoto et al. | |
| 2004/0024341 A1 | 2/2004 | Jacobs | |
| 2005/0010156 A1 | 1/2005 | Lortscher | |
| 2005/0050616 A1 | 3/2005 | Krautbauer | |
| 2005/0177931 A1 | 8/2005 | Tsujimoto | |
| 2005/0204458 A1 | 9/2005 | Wong | |
| 2005/0268387 A1 | 12/2005 | Wong | |
| 2005/0278839 A1 | 12/2005 | Atwater et al. | |
| 2008/0058693 A1 | 3/2008 | Lukens | |
| 2008/0201829 A1 | 8/2008 | Wang | |
| 2008/0254712 A1 | 10/2008 | Christensen | |
| 2009/0241968 A1 | 10/2009 | Murphy et al. | |
| 2010/0024104 A1 | 2/2010 | Sims | |
| 2010/0024105 A1 | 2/2010 | Sims | |
| 2010/0275349 A1 | 11/2010 | Wilson, II | |
| 2010/0275350 A1 | 11/2010 | Wong | |
| 2010/0275351 A1 | 11/2010 | Wong | |

(56) References Cited

U.S. PATENT DOCUMENTS

| | | |
|---|---|---|
| 2011/0009794 A1 | 1/2011 | Diamond et al. |
| 2012/0304364 A1 | 12/2012 | Landi et al. |
| 2013/0117911 A1* | 5/2013 | Nam .................... A41B 9/023 |
| | | 2/403 |
| 2013/0263359 A1 | 10/2013 | Wong |
| 2014/0166024 A1 | 6/2014 | Davidson et al. |
| 2014/0276325 A1 | 9/2014 | Turkbas |

OTHER PUBLICATIONS

International Preliminary Report on Patentability issued in PCT/US2014/026527, dated Sep. 24, 2015, 7 pages.

International Search Report and Written Opinion issued in PCT/US2014/26527, dated Jul. 28, 2014, 13 pages.

Based upon information and belief, the following was publicly accessible prior to Jul. 18, 2012: "Shock Doctor Product Catalog 2012."

* cited by examiner

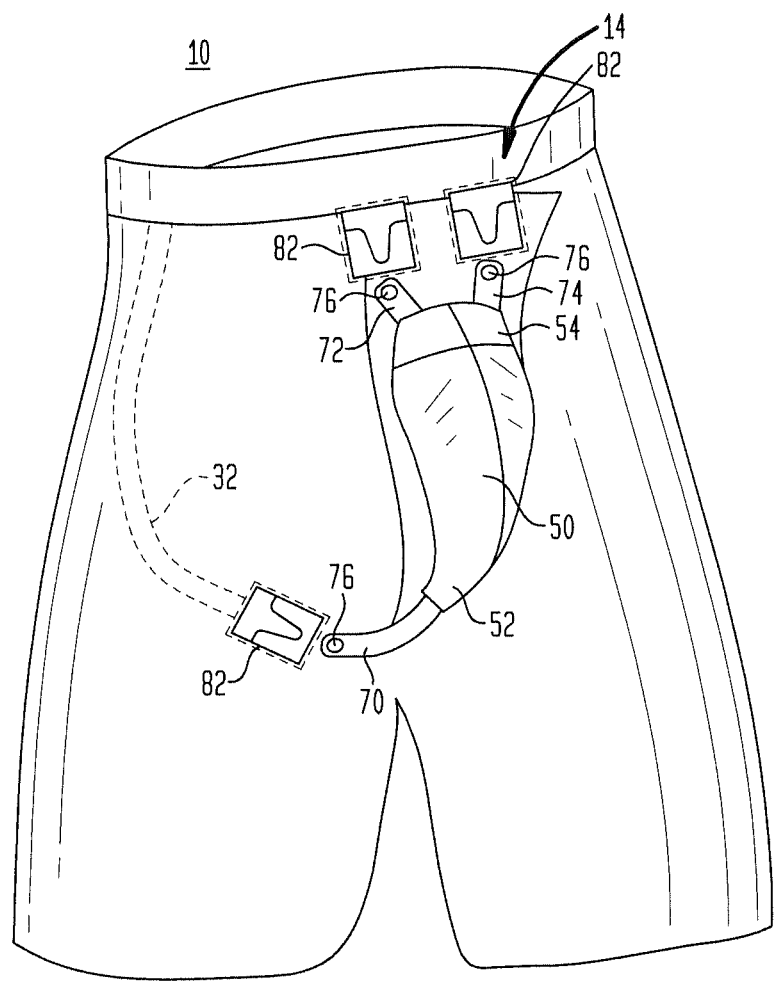
FIG. 5
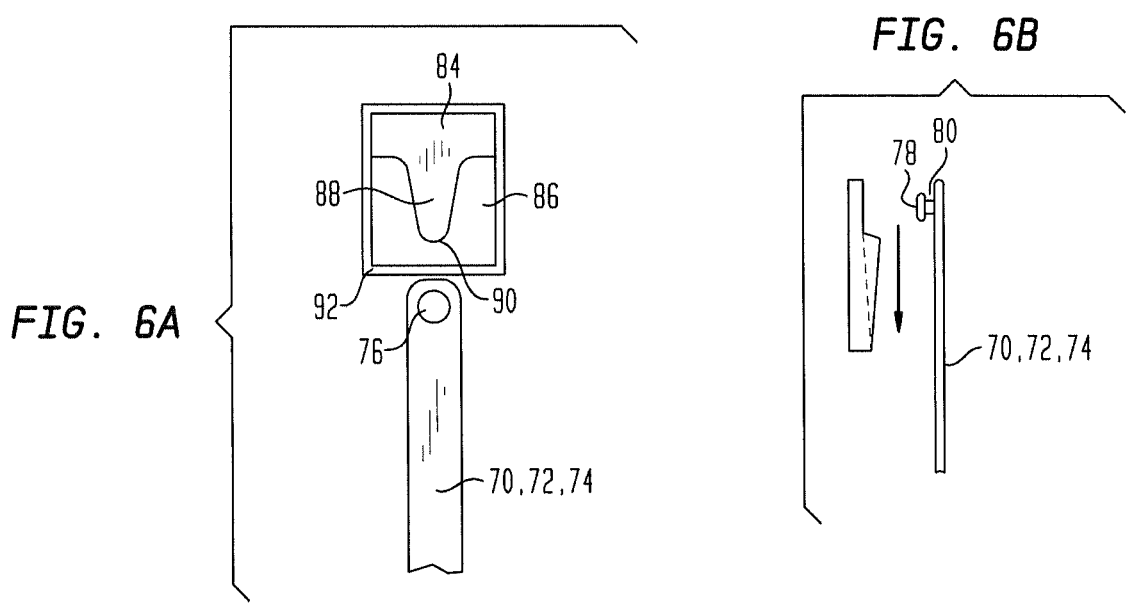
FIG. 6A
FIG. 6B

ATHLETIC GARMENT WITH INTEGRAL CUP ASSEMBLY

CROSS-REFERENCE TO RELATED APPLICATIONS

The present application is a continuation of U.S. patent application Ser. No. 13/551,881, now allowed, filed Jul. 18, 2012, which is a continuation-in-part of U.S. patent application Ser. No. 13/357,955, now allowed, filed Jan. 25, 2012, which claims the benefit of the filing date of U.S. Provisional Patent Application No. 61/479,566, filed Apr. 27, 2011, the disclosures of which are incorporated herein by reference.

BACKGROUND OF THE INVENTION

The present invention generally relates to athletic garments and, more particularly, to an athletic garment with an integral cup or cup assembly for holding an athletic protective device.

In many athletic events, players may suffer injuries in their groin regions as a consequence of impacts to that region. To avoid, or at least minimize injuries in the male groin region, players use different types of protective devices, such as athletic protective cups. Athletic protective cups are typically used in many contact, sports, such as football, baseball, hockey, soccer and the like. Protective cups, however, are also used in non-athletic events where the users are susceptible to impacts to the groin region.

Protective cups should be secured against the user's body to protect the groin region from impact. Several apparatus and devices have been developed over the years to secure a protective cup over a male's genitals. For instance, athletes sometimes use jockstraps to hold a protective cup in place. U.S. Pat. No. 4,134,400 describes an example of a jockstrap. This jockstrap includes a waistband, multiple straps attached to the waistband, and a pouch for holding the protective cup. The pouch is attached to the waistband and to all the straps. The straps are specifically attached to the back portion of the waistband. While the type of jockstrap disclosed in U.S. Pat. No. 4,134,400 can secure a protective cup over the user's groin region, it can be confusing and difficult to put on due to the multiple straps. In order to wear the jockstrap, the user must place his legs through specific straps. However, the user may easily put his legs through the incorrect straps. If the jockstrap is not worn properly, the protective cup may move out of its proper position, leaving the user unprotected from blows to the groin. In addition, the straps of the jockstrap may stretch due to regular wear and tear, becoming incapable of holding the protective cup in the proper position.

Instead of a jockstrap, athletes may use a jock short or brief to secure a protective cup against their bodies. U.S. Pat. Nos. 5,157,793 and 5,819,323 describe jock shorts or briefs capable of holding a protective cup and made of a stretchable fabric, such as the polyurethane-polyurea copolymer fabric, sold under the trademark LYCRA® by Invista North America S.A.R.L. Corporation. These kinds of shorts tightly fit the user's body. Nevertheless, these shorts do not provide enough strength to hold and support the protective cup over the user's groin region. In this type of shorts, gravity and the constant movement by the user may cause the cup to move out of its proper place. In such case, the user may be injured if he receives a blow to his genitals.

Other kinds of jock support shorts may fit loosely the user's body and rely on straps to hold a protective cup in place. U.S. Pat. Nos. 7,757,307 and 7,216,371 describe shorts, which employ straps to support a protective cup. In these types of shorts, the straps are attached to a pocket, which holds the protective cup. These straps suffer from the same shortcomings as the straps of the jockstrap described above. Thus, during use, the protective cup may move out of its proper position.

In light of the shortcomings of current devices for securing a protective cup in its proper place, there is a need for a device, apparatus or garment capable of properly securing and holding a protective device over a wearer's genitals.

BRIEF SUMMARY OF THE INVENTION

The present disclosure relates to athletic garments adapted for supporting and holding a protective device. An embodiment of the athletic garment includes a main body, a pocket, and a resilient strap. The main body has a waistband. The pocket is dimensioned to removeably receive a protective device, such as athletic protective cup, and has one end attached to a portion of the main body. The resilient strap couples another end of the pocket to another portion of the main body.

In another embodiment, the athletic garment generally includes a main body, a pocket, an elastic resilient strap and at least two elastic members. The main body includes a front panel, rear panel, at least two side panels, and a waistband. The waistband extends along the front panel, the rear panel, and the two side panels of the main body. The pocket is dimensioned to removeably receive an athletic protective cup and has an open end, a closed end and two side portions. The open end of the pocket can be attached to an inner portion of the waistband at the front panel of the main body, or to an inner upper area of the front panel of the main body. Alternatively the open end of the pocket can be attached to both locations. The elastic resilient strap couples the closed end of the pocket to the rear panel of the main body along a central axis of the rear panel of the main body. The two elastic members extend along the side portions of the pocket and are extensions of the resilient strap, forming a Y-shaped configuration.

In a further embodiment, the athletic garment generally includes a short member, a pocket, and a resilient strap. The short member includes a front panel, rear panel, at least two side panels, and a waistband. The waistband extends along the front panel, the rear panel, and the two side panels of the short member. The pocket is dimensioned to removeably receive an athletic protective cup, and has an open end, a closed end, and two side portions. The open end is attached to the waistband at the front panel of the short member. The resilient strap couples the closed end of the pocket to the rear panel of the short member, and is attached along a central axis of the rear panel of the short member.

In yet another embodiment, the athletic garment generally includes a main body with a waistband, an athletic protective cup, and a strap. The athletic protective cup has a first end and a second end, with the first end being directly attached to a portion of the main body. The strap couples the second end of the athletic protective device to a rear panel of the main body.

In yet still another embodiment, there is disclosed an athletic garment, comprising: a main body forming an article of wearing apparel; a pocket dimensioned to removeably receive an athletic protective cup, one end of the pocket being coupled to one portion of the main body; and a strap coupling another end of the pocket to another portion of the main body.

In yet still another embodiment, there is disclosed an athletic garment, comprising: a short member forming an article of wearing apparel including a front portion, rear portion, at least two side portions, and a waistband extending along the front portion, the rear portion, and the at least two side portions; a pocket dimensioned to removeably receive an athletic protective cup and having an open end, a closed end and two side portions, the open end being coupled to the waistband at the front portion of the short member; and a strap coupling the closed end of the pocket to the rear portion of the short member, the strap being attached along a central axis of the rear portion of the short member.

In yet still another embodiment, there is disclosed an athletic garment, comprising: a main body forming an article of wearing apparel including a front panel, a rear panel, at least two side panels, and a waistband extending along the front panel, the rear panel, and the at least two side panels of the main body; a pocket dimensioned to removeably receive an athletic protective cup and having an open end, a closed end and two side portions, the open end being attached to at least one of a portion of the waistband at the front panel or an inner upper area of the front panel of the main body; an elastic strap coupling the closed end of the pocket to the rear panel of the main body along a central axis of the rear panel; and at least two elastic members extending along the side portions of the pocket, wherein at least two elastic members are extensions of the strap, the strap having a Y-shaped configuration.

In yet still another embodiment, there is disclosed an athletic garment, comprising: a main body forming an article of wearing apparel; an athletic protective cup having a first end and a second end, the first end coupled to one portion of the main body; and a strap coupling the second end of the athletic protective cup to another portion of the main body.

In yet still another embodiment, there is disclosed an athletic garment, comprising: a short member forming an article of wearing apparel including a front portion, rear portion, at least two side portions, and a waistband extending along the front portion, the rear portion, and the at least two side portions of the short member; an athletic protective cup having a first end and a second end, the first end coupled to at least one of the front portion or the waistband; and a resilient strap coupling the second end of the cup to the rear portion.

In yet still another embodiment, there is disclosed an athletic garment system, comprising: a main body forming an article of wearing apparel; a pocket dimensioned to removeably receive an athletic protective cup, the pocket having an open end and a closed end, the open end coupled to one portion of the main body; a resilient strap coupling the closed end of the cup to another portion of the main body; and an athletic protective cup adapted to be received within the pocket.

In yet still another embodiment, the athletic cup can be used as an incontinent pad during athletic and non-athletic activities. For example, the cup can be formed from cellulose type diaper material for liquid absorption. The cup can be replaceably positioned within the supported pocket of the garment. In another example, the cup can be formed from a soft resilient foam like material into a generally self-sustaining cup shape. An incontinent pad can be removeably attached to the cup to be placed either within a pocket or separately attached to the garment as described above. The incontinent pad can be adhered to the cup using known adhesives and the like.

In yet still another embodiment, there is disclosed an athletic garment comprising a main body forming an article of wearing apparel, the main body having an outer surface and an inner surface; a supporter having a first end and a second end, the supporter arranged overlying the inner surface of the main body with the first and second ends attached to the main body, whereby a portion of the supporter between the first and second ends is unattached to the main body; and at least one first fastener component attached to the supporter; wherein the at least one first fastener component is adapted to be releaseably coupled to a second fastener component attached to an athletic protective cup, whereby the athletic protective cup is removeably attached to the supporter.

In yet still another embodiment, there is disclosed an athletic garment, comprising a main body forming an article of wearing apparel, the main body including a waistband and a rear panel attached thereto; a pocket dimensioned to removeably receive an athletic protective cup through an opening therein, one end of the pocket being coupled to one portion of the main body; and at least first and second straps coupling another end of the pocket to a portion of the rear panel of the main body at spaced apart locations.

An athletic garment comprising a main body forming an article of wearing apparel, the main body having an outer surface and an inner surface; a supporter having a first end and a second end, the supporter arranged overlying the inner surface of the main body with the first and second ends coupled to the main body, whereby a portion of the supporter between the first and second ends is unattached to the main body; at least one first fastener component attached to the supporter, wherein the at least one first fastener component is adapted to be releaseably coupled to a second fastener component attached to an athletic protective cup, whereby the athletic protective cup is removeably attached to the supporter; and a plurality of straps attaching the second end of the supporter to the main body at spaced apart locations.

An athletic garment system, comprising a short member forming an article of wearing apparel including a front portion, rear portion, at least two side portions, and a waistband extending along the front portion, the rear portion, and the at least two side portions of the short member; an athletic protective cup; means for coupling the athletic protective cup to the short member; and a plurality of straps attached to the rear portion of the short member at spaced apart locations and to the means for coupling.

BRIEF DESCRIPTION OF THE DRAWINGS

Various embodiments of the present invention will now be described with reference to the appended drawings. It is appreciated that these drawings depict only exemplary embodiments of the invention and are therefore not to be considered limiting of its scope.

FIG. 5 shows a perspective view of an athletic garment for holding a device such as an athletic protective cup in accordance with a further embodiment of the present invention.

FIGS. 6A and 6B show the construction and operation of the fastening device in accordance with one embodiment of the present invention as shown in FIG. 5.

DETAILED DESCRIPTION

Figure 1:
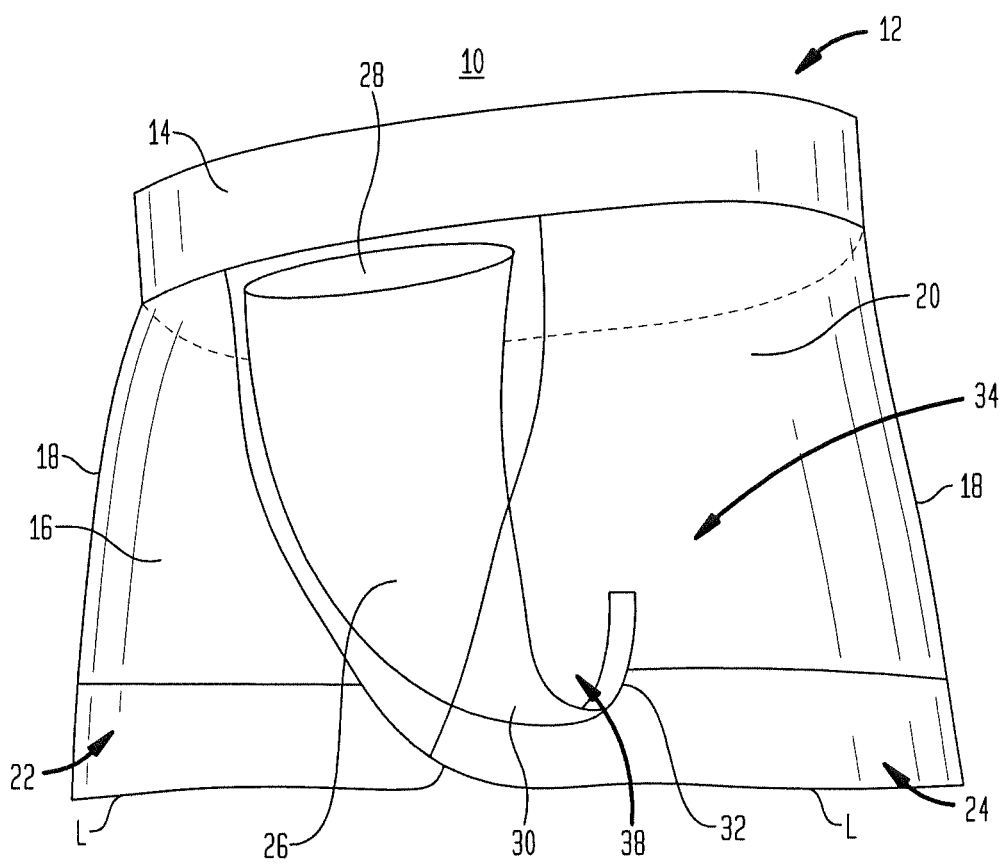
FIG. 1 shows a perspective view of an athletic garment for holding a device for protecting a groin region in accordance with an embodiment of the present invention.

In describing the preferred embodiments of the invention illustrated in the drawings, specific terminology will be used for the sake of clarity. However, the invention is not intended to be limited to the specific terms so used, and it is to be understood that each specific term includes all equivalents that operate in a similar manner to accomplish a similar purpose.

FIG. 1 illustrates an athletic garment 10 such as an article of wearing apparel for holding a device for protecting a user's groin region. The athletic garment may, for example, hold an athletic protective cup, such as the cup described in U.S. Pat. Nos. 6,319,219, 7,712,156 and 7,296,307; and U.S. Patent Publication Nos. 2004/0024341 and 2008/0201829, the entire disclosures of which are herein incorporated by reference. The athletic garment 10 may be jock shorts, sports brief or any other garment capable of securing a protective device over the wearer's groin region.

In some embodiments, the athletic garment 10 includes a short member or main body 12 made of any suitable material, such as fabric which forms an article of wearing apparel. Suitable materials for the main body 12 include, but are not limited to, cotton, polyester, the elastane sold under the trademark LYCRA® by Invista North America S.A.R.L. Corporation, or any combination thereof. For example, the main body 12 may be made of a blend of 90% polyester and 10% elastane. In another embodiment, the main body 12 may be made of a blend of 90% cotton and 10% elastane. Apart from elastane, the main body 12 may be wholly or partly made of any other suitable stretchable material.

The main body 12 of the athletic garment 10 includes, for example, a waistband 14 defining a waist opening dimensioned to receive a user's waist, and a plurality of garment forming portions such as at least one front panel 16, at least one rear panel 20 and at least two sides panels 18. Alternatively, the main body 12 may be made of a one-piece (i.e., monolithic) structure. In such embodiment, the main body 12 may be, for example, knitted together in a unitary (i.e., indivisible) manner thereby forming a front portion, a rear portion and at least two side portions. The waistband 14 may be wholly or partly made of any suitable elastic material to maintain the athletic garment 10 secured against the user's waist. The waistband 14 is attached to and extends along an upper portion of the front panel 16, the rear panel 20 and the two side panels 18.

Each side panel 18 interconnects the front panel 16 and rear panel 20. The front panel 16, the rear panel 20 and the two side panels 18 collectively form leg openings 22 and 24.

Each leg opening 22 and 24 is dimensioned to receive a user's legs L The waist opening defined by the waistband 14 is in communication with the leg openings 22 and 24 to allow a user to put on the athletic garment 10.

The main body 12 of the athletic garment 10 further includes a bottom portion 38 disposed between the leg openings 22 and 24. The bottom portion 38 extends between the front panel 16 and rear panel 20.

In addition to the main body 12, the athletic garment 10 includes a pouch or pocket 26 positioned over a central inner surface of the front panel 16. The pocket 26 has a first open end 28 and a second generally closed end 30. The first open end 28 leads to an inner cavity of the pocket 26. The inner cavity and the first open end 28 of the pocket 26 are each dimensioned to receive a protective device, such as an athletic protective cup. The inner cavity of the pocket 26 may be specifically adapted and dimensioned to hold the athletic protective cup described in U.S. Pat. No. 6,319,219 or those disclosed in the aforementioned patents and patent publications. In order to hold the athletic protective cup described in U.S. Pat. No. 6,319,219, the pocket 26 may have a substantially triangular shape. As such, the width of the pocket 26 may be greater at its first open end 28 than at its second closed end 30.

Most of the pocket 26 is disposed freely over a central inner surface of the front panel 16. Only the first open end 28 and the second closed end 30 of the pocket 26 are connected to another portion of the athletic garment 10. The remaining portions of the pocket 26 are not connected to the main body 12 of the athletic garment 10. Consequently, the pocket 26 may move (to a certain extent) relative to the main body 12 of the athletic garment 10 when worn.

To allow the pocket 26 to move relative to the main body 12, the first open end 28 may be attached to an inner portion of the waistband 14 and/or an inner upper area of the front panel 16. In some embodiments, the first open end 28 of the pocket 26 is not attached to the front panel 16; rather, the first open end 28 is solely attached to an inner portion of the waistband 14. Alternatively, the first open end 28 of the pocket 26 is exclusively attached to an upper inner portion of the front panel 16. In a further embodiment, the first open end 28 of the pocket 26 is only attached to an inner portion of the waistband 14 and to an upper inner portion of the front panel 16. The pocket may also be releaseably attached to allow replacement of the pocket should it become worn or damaged, or one of a different size to accommodate a smaller or larger protective cup.

Aside from the first open end 28, the other portion of the pocket 26 attached to the main body 12 is the second generally closed end 30 in the embodiment depicted in the FIG. 1. Other embodiments may nonetheless have more portions of the pocket 26 attached to the main body 12 of the athletic garment 10.

As shown in FIG. 1, a resilient or elongate member 32 may connect the second closed end 30 of the pocket 26 to a portion of the rear panel 20. The resilient member 32 may have an elongated shape and may be wholly or partly made of any suitable elastic or resilient material. Alternatively, member 32 may be wholly or partly made of a non-elastic or non-stretchable material. In one embodiment, the resilient, member 32 may be a single monolithic band or strap. Alternatively, the resilient member 32 may be may be formed by a plurality of discrete resilient elements connected to one another. The color of the resilient member 32 may be different from the color of the main body 12 to enhance the visibility of the resilient member 32. For example, the resilient member 32 may be green, while the main body 12 may be white. The resilient member 32 may also be a different color from the pocket 26.

In some embodiments, the resilient member 32 may be specifically attached to a bottom inner portion 34 of the rear panel 20. The bottom inner portion 34 of the rear panel 20 may be located adjacent the bottom portion 38 and along a central axis C extending along the middle of rear panel 20, so that a portion of the resilient member 32 extends between the user's legs when in use. The portion of the resilient member 32 between the second closed end 30 of the pocket 26 and the bottom inner portion 34 of the rear panel 20 is not attached to any other part of the main body 12 of the athletic garment 10. As a result, the pocket 26 may move relative to the main body 10 whenever the user plays, twists, turns or crouches, while the resilient member 32 biases the pocket 26 towards the wearer's groin, thereby maintaining the protective cup inside the pocket 26 securely positioned over the user's genitals. In other words, the resilient member 32 biases the pocket 26 toward the user's groin so that the protective cup inside the pocket 26 is pressed against the pubic bone.

Figure 2:
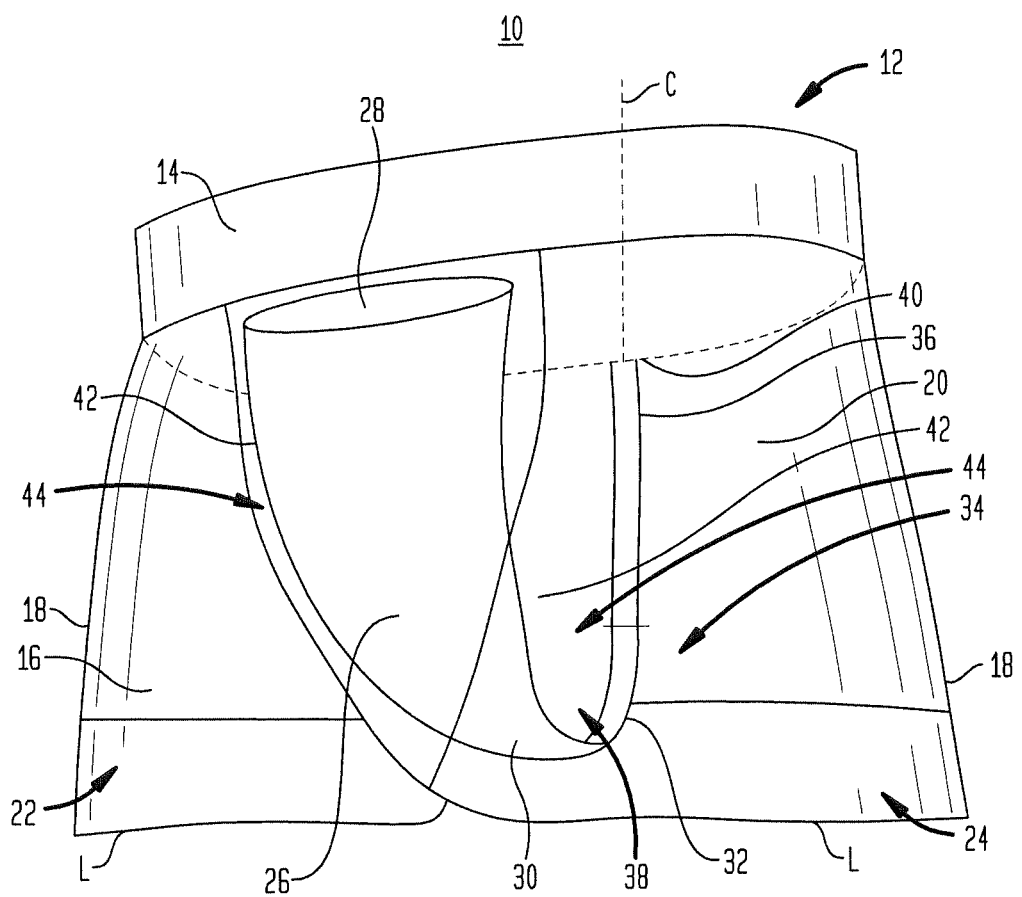
FIG. 2 shows a perspective view of an athletic garment for holding a device for protecting a groin region in accordance with another embodiment of the present invention.
Figure 9:
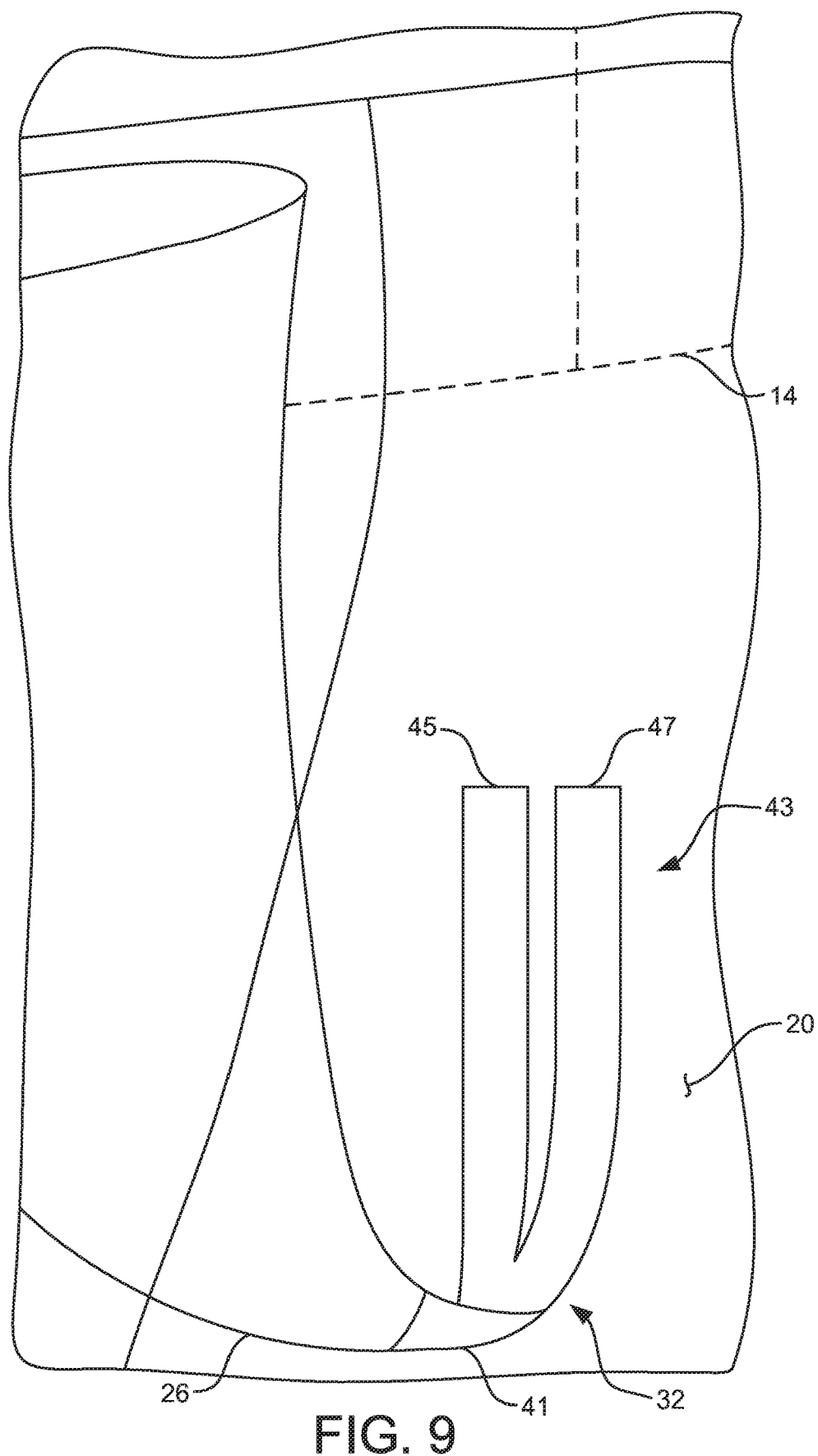
FIG. 9 shows a partial perspective view of an athletic garment for removeably securing an athletic protective cup in accordance with a further embodiment of the present invention.

With reference to FIG. 2, the resilient member 32 may further include an extended rear portion 36 attached to the rear panel 20 along central axis C. The rear portion 36 may be monolithically formed with the other portions of the resilient member 32. In certain embodiments, the rear portion 36 of resilient member 32 may be attached to the rear panel 20 from the bottom inner portion 34 to an upper edge 40 of the rear panel 20 adjacent to the waistband 14 along central axis C. A seam may be disposed along at least a portion of the central axis C. Accordingly, the rear portion 36 of the resilient member 32 may be connected to a seam of the rear panel 20. In an alternate embodiment, the rear portion 36 of the resilient member 32 may not reach the upper edge 40 of the rear panel 20. Rather, the rear portion 36 of the resilient member 32 only extends to a part of the rear panel 20 spaced apart from the waistband 14. With reference to FIG. 9 and as an example of such an alternate embodiment, the resilient member 32 forms a "Y"-shape with a first end 41 corresponding to a bottom of the "Y"-shape and directly attaching to the bottom of the pocket 26. The first end 41 extends toward the rear panel 20, and the resilient member 32 branches into a second end 43 corresponding to a top of the "Y"-shape. The second end 43 terminates and directly attaches to the rear panel 20 at a first location 45 spaced apart from the waistband 14 and terminates and directly attaches to the rear panel 20 at a second location 47 spaced apart from the waistband 14.

In addition to the resilient member 32, the athletic garment 10 may include elastic members 42 extending along the side portions 44 of the pocket 26. Each side portions 44 of the pocket 26 extends generally from the first open end 28 to the second closed end 30. The elastic members 42 may be extensions of the resilient member 32. In such case, the resilient member 32 has a substantially Y-shaped configuration. Accordingly, the elastic members 42 are monolithically formed with the resilient member 32. Alternatively, the elastic members 42 may be discrete elements, such as elastic bands, attached to the side portions 44 of the pocket 26. As such, the elastic members 42 may be connected to the resilient member 32 at or near the second closed end 30 of the pocket 26. However, the elastic members 42 may not be connected at all to the resilient member 32.

The elastic members 42 may take many forms. For instance, the elastic members 42 may include elastic stitching alongside the side portions 44 of the pocket 26. In another embodiment, the elastic members 42 may include elastic elongated elements or bands attached to the side portions 44 of the pocket 26. These elongated elements or bands may be disposed inside and/or outside the side portions 44 of the pocket 26. In some embodiments, the elastic stitching may be combined with the elongated band to form the elastic elements 44. Moreover, the elastic members 42 may be monolithically formed with the side portions 44 of the pocket 26. In this case, the side portions 44 themselves are wholly or partly made of an elastic material. Regardless of their form, the elastic members 42 help maintain the athletic protective cup inside the pocket 26 in the proper position (i.e., over the user's genitals.)

During use, a user may position a protective device, such as an athletic protective cup, inside the pocket 26 before or after putting on the athletic garment 10. To put on the athletic garment 10, the user may simply inserting one leg through leg opening 22 and the other leg through leg opening 24. Then, the user pulls the athletic garment 10 towards the head until the waistband 14 is positioned around the waist. The user should make sure that the pocket 26 is placed over the genitals. At this point, the resilient member 32 should be positioned between the user's legs. Since the athletic garment 10 does not have multiple straps, the user may put it on without much difficulty.

Once the user has properly put on the athletic garment 10, the pocket 26 can move relative to the main body 12 as the user moves. Irrespective of how the user moves, the resilient member 32 pulls the pocket 26 toward the groin and therefore keeps the protective device in its proper position (i.e., over the wearer's genitals.) As a result, the user will be protected from impacts to his genitals since the protective device will be positioned over his groin.

In another embodiment, the cup as described can function as an incontinent device. For example, the cup can be formed as an interchangeable soft cup of absorbent material such as from synthetic polymers and/or cellulose type diaper material. The cup can be formed into a self-sustaining cup shape such as by molding to be inserted into the pocket 26. Such a cup would likely be disposable. The cup can also be formed as a soft cup from thermoplastic elastomers, e.g., polyethylene, polyurethane, polypropylene, ethylene, vinyl acetate and the like. A soft absorbent material such as noted above can be releaseably attached to the soft cup to be inserted into the pocket 26. The soft two piece cup can be reuseable or disposable. It is also contemplated that an absorbent pad in general can be sized and shaped to be removeably inserted into the pocket 26.

Figure 3:
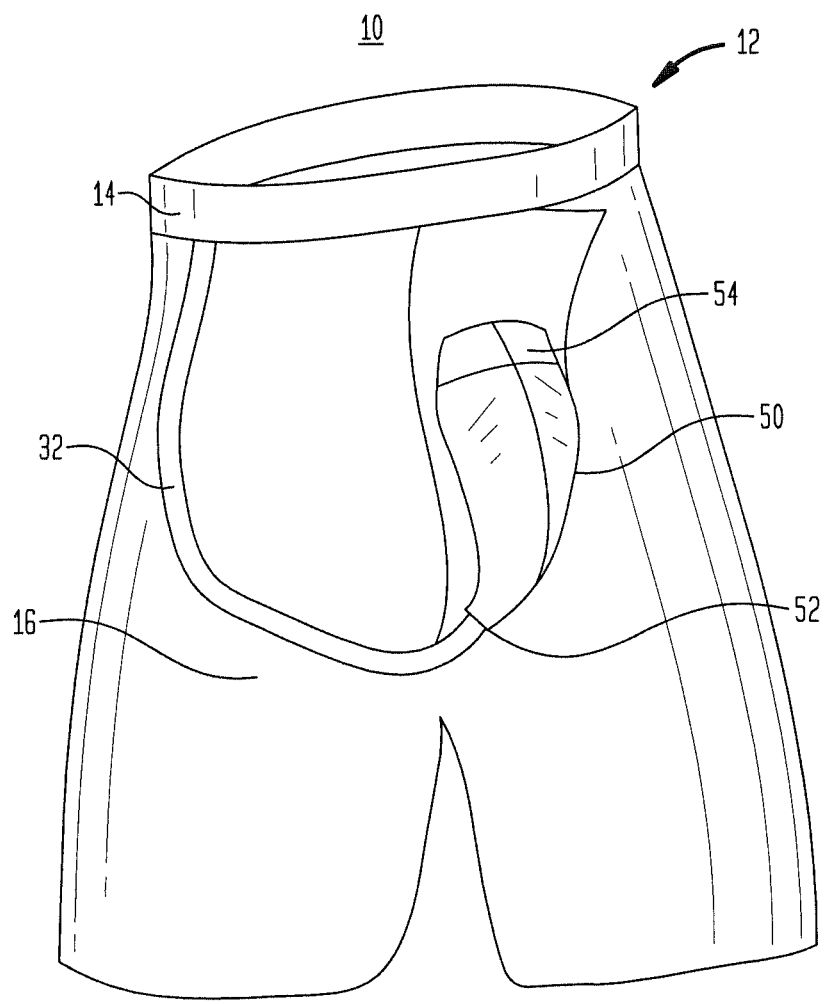
FIG. 3 shows a perspective view of an athletic garment for holding a device for protecting a groin region in accordance with a further embodiment of the present invention.

FIG. 3 illustrates a further embodiment of an athletic garment 10 for holding a device for protecting a user's groin region. In this illustrative embodiment, the short member or main body 12 includes a cup 50, such as the cup described in U.S. Pat. No. 6,319,219, attached to or otherwise coupled to the main body 12 without any required pocket or pouch. The cup 50 has a lower portion 52 and an upper portion 54. The lower portion 52 of the cup 50 may be removeably attached to the resilient member 32. This may be accomplished, for example, by using VELCRO® (i.e., a type of hook-and-loop fastener), snaps, hooks or other releasable type fasteners. Alternatively, the lower portion 52 of cup 50 may be non-removeably attached to resilient member 32. This may be accomplished, for example, by stitching, bonding, mechanically fastening and the like the lower portion 52 of cup 50 to the resilient member 32.

Figure 4:
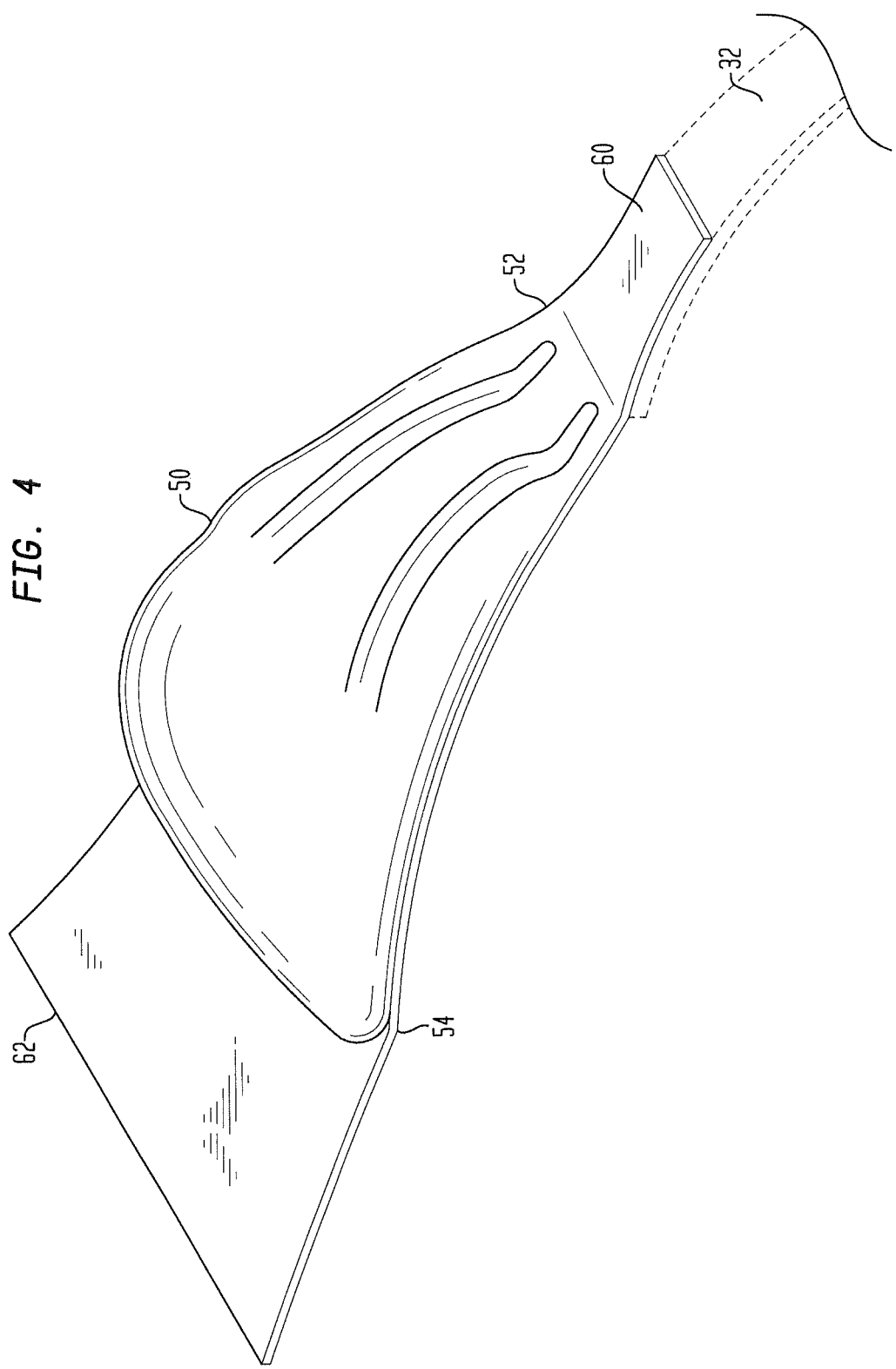
FIG. 4 shows a perspective view of an athletic protective cup in accordance with an embodiment of the present invention.

In an alternative embodiment shown in FIG. 4, the lower portion 52 of the cup may be provided with an extension 60. The extension may be in the form of a flat or planar member of suitable dimensions. The extension 60 may be formed integral as one piece with the cup 50. The extension may also be formed as a separate member attached to the cup 50 such as by stitching, bonding, mechanical fastening and the like. The extension can be made from various material, such as polymer flexible sheets, soft elastic material (e.g., thermoplastic elastomers) synthetic and natural fabrics, and the like. The extension can be removeably or fixedly attached to the resiliant member 32 in the manner as previously described with respect to the cup 50. The resiliant member 32 may be attached to the cup 50 along its longitudinal axis, which will preferably be coincident with the central axis of the rear portion or panel of the athletic garment 10.

The upper portion 54 of cup 50 as shown in FIG. 3 may similarly be removeably or non-removeably attached to the main body 12. The site of attachment of the top portion 54 of cup 50 to the main body 12 may be, for example, at the inner side of a front portion of waistband 14 or at an inner upper portion of the front panel 16 spaced away from the waistband 14. The upper portion 54 of cup 50 may be stitched, bonded or otherwise attached directly to an inner upper portion of the front panel 16.

Alternatively as shown in FIG. 4, an extension 62 to the upper portion 54 of cup 50 may be provided, the extension being removeably or non-removeably attached to either an inner upper portion of the front panel 16 or to the inner side of a front portion of waistband 14, for example by stitching or VELCRO®, or by other fastening means. The extension 62 may be formed and constructed in a similar manner as extension 60 previously described. These methods of attachments as thus far described are illustrative only, and one skilled in the art would recognize that any secure removable or non-removable method of attaching the cup 50 to the main body 12 is within the scope of this invention.

The cup 50 as shown in the embodiments of FIGS. 3 and 4 can also be constructed to function as an incontinent device as previously described. In this regard, the cup can be formed as an interchangeable soft cup of absorbent material or as a soft cup from thermoplastic elastomers with an adhered absorbent material. The incontinent cup can be fixedly or releaseably attached to the garment in the manner as thus far described in any of the above embodiments.

Referring now to FIG. 5, there will be described the construction of a fastening device for releaseably securing a cup 50 to the garment 10 in accordance with another embodiment of the present invention. An extension 70 is attached to the lower end 52 of the cup 50, while a pair of spaced apart extensions 72, 74 are attached to the upper portion 54 of the cup. Each of the extensions 70, 72, 74 can be constructed in the nature of, for example, elongated straps formed from soft elastic material such as molded thermoplastic elastomers of the type hereinbefore described. The extensions 70, 72, 74 can be integrally molded with the cup 50 or formed separately therefrom and attached thereto by any suitable means such as thermal bonding, stitching, mechanical fastening, adhesive bonding and the like. Extensions 72, 74 can be formed as a single extension such as the single extension 62 shown in FIG. 4.

The free end of each extension 70, 72, 74 supports a male snap head 76 which may be separately or integrally formed with each of the extensions by molding from, for example, the aforementioned polymers including thermoplastic elastomers. As best shown in FIG. 6B, each of the snap heads 76 include an enlarged head 78 forming an undercut 80. In the preferred embodiment, the head 78 is circular in nature, thereby forming a circular undercut 80 circumscribing the head. Although the head 78 has been described as circular, other shapes such as oval, polygon, square and the like can be suitably used.

Each of the snap heads 76 releaseably engage a female component 82. As best shown in FIG. 6A, the female components 82 are constructed from a rear panel 84 and an attached overlying front panel 86 having a u-shaped opening 88. The peripheral edges of the rear and front panels 84, 86 are secured to each other to form an integral unit. In the preferred embodiment, the female component 82 is formed from soft thermoplastic elastomeric material such as by molding and the like. In this regard, the rear panel 84 and overlying front panel 86 can be integrally formed with one another in a single molding process. Otherwise, the rear panel and overlying front panel can be bonded peripherally to each other such as by stitching, adhesive bonding, thermal bonding and the like. The u-shape opening 88 has an enlarged entrance opening, slightly tapering to the opening's closed end 90. The width of the closed end 90 is approximately the same as that of the undercut 80 in the snap heads 76.

The female components 82 are secured to the garment 10 at their appropriate location for alignment with the corresponding snap heads 76 for proper placement and positioning of the cup 50. For example as shown in FIG. 5, a pair of spaced apart female components 82 may be adhered to a region of the garment 10 proximate the waist band 14 and another female component proximate to the resilient member 32. It is also contemplated that the female component 82 can be secured directly to the free end of the resilient member 32, as opposed to being attached directly to the garment 10. The female components 82, in accordance with the preferred embodiment, can be stitched about their peripheral edge 92 which provides a stitching area for adhering the female component to the garment 10.

As shown in FIGS. 6A, 6B, the snap head 76 can be removeably attached to the female component 82 in a simple manipulation of the snap head. In this regard, the head 76 is initially positioned within the u-shaped opening 88, with the edges thereof in alignment with the undercut 80. As the snap head 76 is slid or displaced along the length of the opening 88, the narrowing of the opening causes the edges thereof to be received within the undercut 80 of head 78 as the head approaches the closed end 90. In this position, the snap head 76 is firmly releaseably engaged by the female component 82. This engagement can be easily accomplished by the user's manipulation with one's fingers either directly with the snap heads 76 or by pulling on each of the extensions 70, 72, 74. The snap head 76 can be released from the female components 82 in a reverse motion from that previously described.

The snap head 76 and female components 82 as thus far described can also be used in the aforementioned embodiments with respect to the use of the present invention with an incontinent pad. For example, the extensions 70, 72, 74 can be integrally formed with the soft resilient foam like material forming the incontinent pad receiving cup. The free end of each extension will be provided with a male snap head 76, either integrally formed therewith or attached thereto. The snap head 76 can be replaced by any other suitable type fastener, such as hooks, VELCRO® type fasteners, snaps, eyelets, catches and the like.

Figure 7:
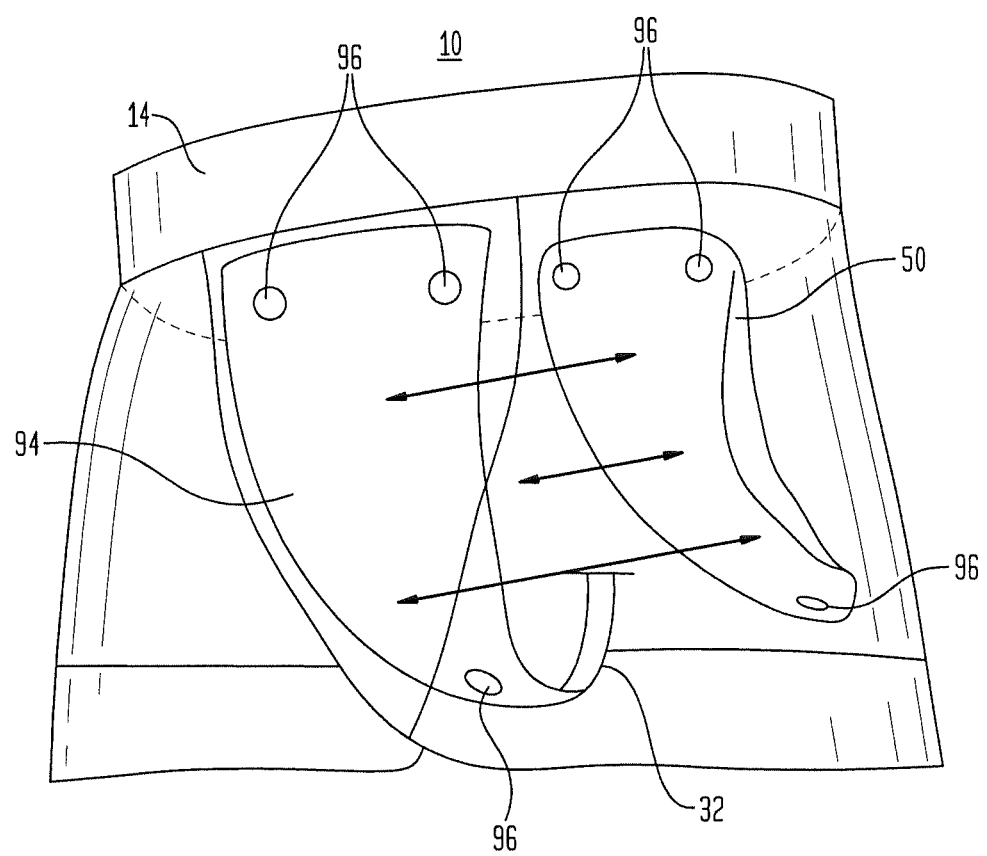
FIG. 7 shows a perspective view of an athletic garment for removeably securing an athletic protective cup in accordance with a further embodiment of the present invention.

Referring to FIG. 7, there is disclosed another embodiment of the present invention. The garment 10 is provided with a supporter 94 instead of the pocket 26 as thus far described. The supporter can be formed from single or multiple layers or panels of fabric of other material which function to provide anatomical support as is typical of jock straps. The supporter may be sewn or otherwise attached to the garment in the manner as previously described with respect to the pocket 26. By way of example, the upper portion of the supporter 94 may be sewn to the garment at or adjacent to the waistband 14. The other end of the supporter 94 can be attached to the resilient member 32 as thus far described.

A cup 50 can be releaseably attached to the supporter 94 using any suitable releasable fastener. By way of example, fasteners 96 in the nature of female/male snaps 96. The snaps 96 may be of the well-known garment type, or any other suitable type fastener, such as hooks, VELCRO® type fasteners, eyelets, catches, etc. In addition, it is contemplated the use of the snap head 76 in combination with female component 82 as described with respect to FIGS. 5, 6A, 6B. The mating female/male components of the snaps 96 are respectively attached to the supporter 96 and to the cup 50. With respect to the supporter 94, the snaps 96 may be sewn into the supporter facing the wearer. With respect to the cup 50, the snaps 96 can be formed into the outer surface of the cup or otherwise attached thereto by any suitable well-known manufacturing techniques.

In use, the wearer can easily attach the cup 50 to the supporter 94 using the plurality of releasable snaps 96. The cup can be easily removed whereby the garment 10 can be laundered or for cup replacement if required in the case of the cup being damaged or worn.

Figure 8:
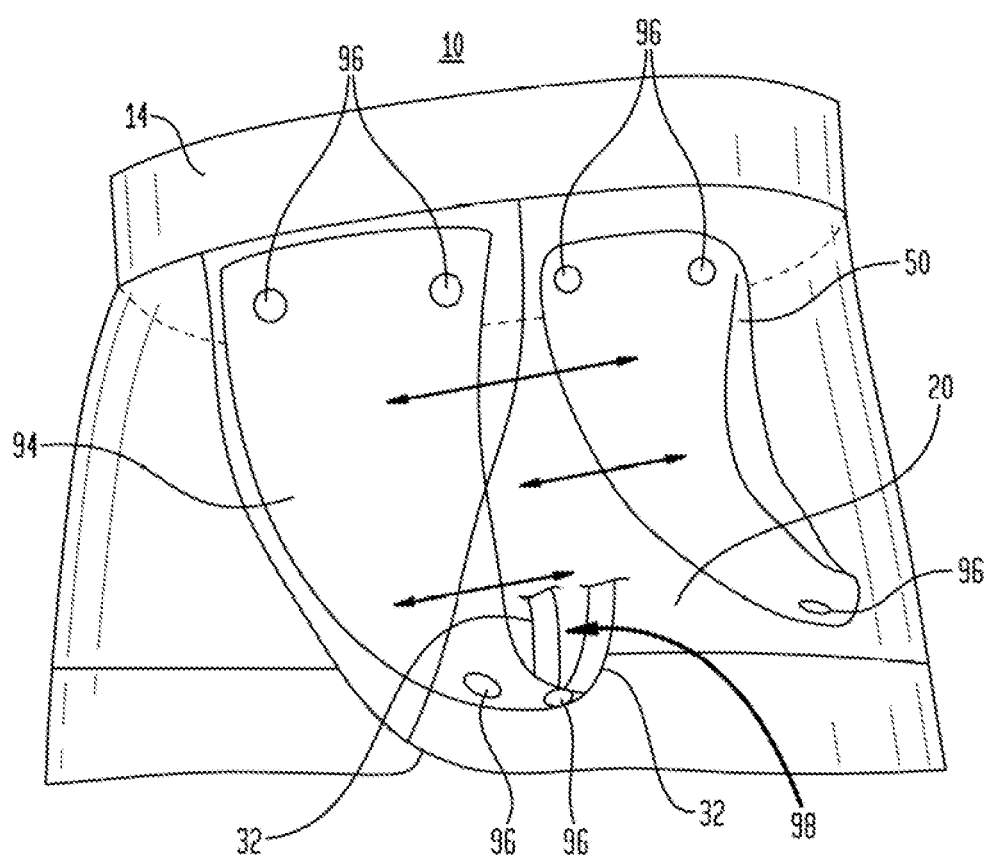
FIG. 8 shows a perspective view of an athletic garment for removeably securing an athletic protective cup in accordance with a further embodiment of the present invention.

Referring to FIG. 8, there is disclosed another embodiment of the present invention. The garment 10 is provided with a supporter 94 as described with respect to FIG. 7, instead of a pocket 26. As previously described, one end of the supporter 94 is attached to a portion of the rear panel 20 of the garment by an elongated member. An athletic protective cup 50 can be releasably attached to the supporter 94 using any suitable releasable fastener.

To enhance maintaining the position of the supporter 94 and the attached cup 50 in the appropriate location within the garment 10, a plurality of elongated members in the form of elongated straps 32 may be used. As shown, a pair of straps 32 have one free end attached to the free end of the supporter 94 which may be along its longitudinal axis. The other free ends of the straps 32 are attached to a portion of the rear panel 20 at spaced apart locations below the waistband 14. For example, the straps 32 may be secured to the rear panel 20 at a location between the bottom of the rear panel and a location of the rear panel spaced from the waistband 14. The straps 32 form an angle 98 therebetween which may be an acute angle, by way of one example less than 45 degrees. By virtue of the acute angle 98, the straps 32 will be positioned between a user's legs when the garment 10 is worn. As such, it is not required that a user position one leg between the straps.

In one embodiment, the straps may be attached by permanently affixing the straps to the free end of the supporter 94 such as by stitching, adhesive bonding and the like. The free ends of the straps 32 may be attached together, and then attached to the free end of the supporter 94 as a unitary member, or separately attached thereto using any suitable attachment means. In other embodiments, the straps 32 may be releasably attached to the supporter 94 using any suitable releasable type fastener, such as fasteners 96 (see FIG. 7) or the combination of a snap head 76 and female component 82 (see FIG. 5). Likewise, the other ends of the straps 32 may be permanently or releasably attached to the rear panel 20 of the garment 10 using any such means, such as permanently stitching, adhesive bonding or releasable type fasteners and the like.

The use of two elongated straps 32 has thus far been described with respect to the embodiment of FIG. 8. However, it is to be understood that the use of a plurality of straps including two or more straps can also be incorporated into the FIGS. 1 and 2 embodiments with respect to pocket 26, coupled to the cup 50 as in the FIGS. 3-6 embodiments, as well as any other embodiments as thus far described in the pending application. In addition, although the present embodiment of FIG. 8 has been described with respect to two elongated straps 32, is contemplated that a greater number of straps may be incorporated for attaching the free end of the supporter 94, pocket 26 or cup 50 to the rear panel 20 of the garment 10. In addition, the straps 32 may be resilient in nature by possessing elastic properties thereby stretching upon movement of the wearer of the garment 10, or alternately, not being resilient and stretchable.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. An athletic garment comprising:
   an upper portion having a front and a rear, a first side and a second side, an interior and an exterior, and a waistband, the upper portion being configured to receive a waist of a user;
   a first leg portion extending downwardly from the upper portion and configured to receive a first leg of the user;
   a second leg portion extending downwardly from the upper portion and configured to receive a second leg of the user;
   a pocket disposed in the interior of the upper portion, the pocket having a first side, a second side, a top, and a bottom, and narrowing in width from the top to the bottom, the first and second sides of the pocket being partially secured to the front of the upper portion within the interior of the upper portion such that the bottom of the pocket is freely suspended from the front of the upper portion; and
   an elongated member extending from the bottom of the pocket to the rear of the upper portion, wherein the elongated member forms a "Y"-shape with a first end of the elongated member corresponding to a bottom of the "Y"-shape, the first end of the elongated member directly attaching to the bottom of the pocket and extending therefrom toward the rear of the upper portion, and the elongated member branching into a second end corresponding to a top of the "Y"-shape, the second end terminating and directly attaching to the rear of the upper portion at a first location spaced apart from the waistband and terminating and directly attaching to the rear of the upper portion at a second location spaced apart from the waistband.

2. The athletic garment of claim 1, wherein the pocket defines an opening near the top of the pocket, and the pocket is sized to receive an athletic protective cup.

3. An athletic garment comprising:

an upper portion having a front and a rear, a first side and a second side, and an interior and an exterior, and a waistband, the upper portion being configured to receive a waist of a user;

a first leg portion extending downwardly from the upper portion and configured to receive a first leg of the user;

a second leg portion extending downwardly from the upper portion and configured to receive a second leg of the user;

a pocket disposed in the interior of the upper portion, the pocket having a first side, a second side, a top, and a bottom, and narrowing in width from the top to the bottom, the first and second sides of the pocket being partially secured to the front of the upper portion within the interior of the upper portion such that the bottom of the pocket is freely suspended from the front of the upper portion; and an elongated member extending from the bottom of the pocket to the rear of the upper portion, wherein the elongated member forms a "Y"-shape with a first end of the elongated member corresponding to a lower leg of the "Y"-shape, the first end of the elongated member directly attaching to the bottom of the pocket, a second end of the elongated member corresponding to a first upper arm of the "Y"-shape, the second end of the elongated member directly attaching to the rear of the upper portion at a first location spaced apart from the waistband, and a third end of the elongated member corresponding to a second upper arm of the "Y"-shape, the third end of the elongated member directly attaching to the rear of the upper portion at a second location spaced apart from the waistband.

* * * * *